United States Patent [19]

Miyanaga et al.

[11] Patent Number: 5,621,055
[45] Date of Patent: Apr. 15, 1997

[54] PROCESS FOR PRODUCING POLYMER PARTICLES WITH IRREGULAR SHAPE

[75] Inventors: Seiichi Miyanaga; Yoshimitsu Ina; Takahide Minami; Takayuki Amiya, all of Wakayama, Japan

[73] Assignee: Kao Corporation, Tokyo, Japan

[21] Appl. No.: 530,759

[22] Filed: Sep. 19, 1995

Related U.S. Application Data

[63] Continuation of Ser. No. 111,437, Aug. 25, 1993, abandoned.

[30] Foreign Application Priority Data

Sep. 10, 1992 [JP] Japan .................................. 4-242219

[51] Int. Cl.$^6$ .................................. C08F 2/20; C08F 2/18
[52] U.S. Cl. .................. 526/225; 526/222; 526/910; 526/923
[58] Field of Search .................. 526/225, 222, 526/910, 923

[56] References Cited

U.S. PATENT DOCUMENTS

| | | |
|---|---|---|
| 3,755,282 | 8/1973 | Wright .................................. 526/909 |
| 4,076,677 | 2/1978 | Sekmakas . |
| 4,340,706 | 7/1982 | Obayashi .............................. 526/207 |
| 4,539,368 | 9/1985 | Duncan et al. . |
| 4,839,395 | 6/1989 | Masamizu ............................ 521/56 |
| 4,880,886 | 11/1989 | Kondo .................................. 526/80 |
| 4,973,632 | 11/1990 | Nagasuna ............................. 526/200 |
| 5,104,764 | 4/1992 | Wada .................................... 430/109 |
| 5,180,798 | 1/1993 | Nakamura ........................... 526/66 |

FOREIGN PATENT DOCUMENTS

| | | |
|---|---|---|
| 57-167302 | 10/1982 | Japan . |
| 61-200102 | 9/1986 | Japan . |
| 62-106902 | 5/1987 | Japan . |

*Primary Examiner*—Fred Zitomer
*Attorney, Agent, or Firm*—Birch, Stewart, Kolasch & Birch, LLP

[57] ABSTRACT

A process for producing polymer particles with an irregular shape by polymerizing a water-soluble polymerizable monomer in a system comprising a hydrophobic organic solvent inert to the polymerization and an aqueous solution of the water-soluble polymerizable monomer, characterized in that the system further contains an anionic surfactant.

6 Claims, 1 Drawing Sheet

PROCESS FOR PRODUCING POLYMER PARTICLES WITH IRREGULAR SHAPE

This application is a continuation, of application Ser. No. 08/111,437 filed on Aug. 25, 1993, now abandoned.

BACKGROUND OF THE INVENTION

1. Field of the Invention

The present invention relates to a process for producing polymer particles with an irregular shape useful as a water-absorbent resin having a small apparent specific gravity and being excellent in water absorption, gas permeability and liquid permeability and also in gel strength after water absorption.

2. Description of the Prior Art

Water-absorbent resins have found a wide variety of applications in the medical service field, such as in sanitary materials, in the food industry and in agricultural technology, etc., because of their capabilities of water absorption and water retention. In particular, when the absorbent resins are used in sanitary materials, such as sanitary articles, disposable diapers, etc., a large water absorption per unit weight and a high absorption rate are required. The water absorption depends upon the molecular structure of the resin, and it is considered that, among the resins having the same weight, the smaller the particle diameter of the resin powder, the larger the specific surface area and the higher the water absorption rate. For this reason, various proposals have been made for a process for producing a water-absorbent resin comprising a resin powder having a small particle diameter and being suitable for a water-absorbent resin.

For example, Japanese Patent Laid-Open No. 167302/1982 proposes an attempt to improve the water absorption rate conducting polymerization using a particular surfactant as a dispersion stabilizer for the polymerization to provide a water-absorbent resin powder having a particle size reduced to 1 to 40 µm. However, mere pulverization of the water-absorbent resin causes the formation of curd during water absorption, so that sufficient water absorption rate cannot be attained.

Japanese Patent Laid-Open No. 106902/1987 describes a process for producing a water-absorbent porous polymer having pores in the inside thereof and a high specific surface area, which comprises preparing an O/W/O emulsion of a monomer and polymerizing the monomer. In this process, however, the step of preparing the O/W/O emulsion is troublesome, and the pores of the resultant polymer are not always interconnected with each other, so that no water-absorbent resin having a satisfactory initial water absorption rate can be produced.

On the other hand, Japanese Patent Laid-Open No. 200102/1986 proposes a process for producing water-absorbent resin particles, which comprises initiating W/O type reverse phase suspension polymerization at 0° to 20° C., holding the reaction system at that temperature until the degree of polymerization reaches 30%, and raising the temperature to complete the polymerization. It discloses that this process provides water-absorbent resin particles wherein fine particles having a size of 1 to 40 µm are relatively loosely bonded to each other and the particles have a high void fraction, are porous and have a high water absorption rate. In this process, it is necessary above all to control the polymerization temperature to be in the range of 0° to 20° C. until the conversion reaches 30%. It is very difficult, however, to control the polymerization temperature by efficiently removing the heat of polymerization at such a low temperature, which renders this process unsuitable for the mass production of water-absorbent resin particles. Further, the process is disadvantageous in that it is poor in productivity, because a large amount of the polymer deposits on a polymerization tank during the course of the reaction.

SUMMARY OF THE INVENTION

Accordingly, an object of the present invention is to provide a process for producing polymer particles with an irregular shape useful as a water-absorbent resin having a small apparent specific gravity and being excellent in water absorption capacity properties, such as initial water absorption rate, gas permeability and liquid permeability and also in gel strength after water absorption, which process is simple in operation and excellent in productivity, and enables the polymer particles to be mass produced.

The present inventors have made intensive studies and, as a result, have discovered that the above-described object can be attained by polymerizing a water-soluble polymerizable monomer in the presence of an anionic surfactant.

The present invention has been made based on the above-described discovery provides a process for producing polymer particles with an irregular shape by polymerizing a water-soluble polymerizable monomer in a system comprising a hydrophobic organic solvent inert to the polymerization and aqueous monomer solution, which process is characterized in that the system further contains an anionic surfactant.

The polymer particles with an irregular shape produced by the process of the present invention comprise a polymer with an irregular shape which is nonspherical and has an average particle diameter of 10 µm or more as measured by sieving (JIS sieve) and a high void fraction, which contributes to a high water absorption rate and excellent gas permeability, liquid permeability and gel strength after water absorption in the water-absorbent resin comprising the polymer particles with an irregular shape.

According to the present invention, it is possible to produce polymer particles with an irregular shape useful as a water-absorbent resin having a small apparent specific gravity and being excellent in water absorption capacity properties, such as initial water absorption rate, gas permeability and also excellent in gel strength after water absorption, through a simple operation at an excellent productivity in a mass-producible manner by polymerizing a water-soluble polymerizable monomer in the presence of an anionic surfactant.

Therefore, the polymer having an irregular shape produced according to the method of the present invention is useful as a water-absorbent polymer to be used in sanitary materials which come in contact with the human body by virtue of its particularly excellent water absorption. Examples of applications include sanitary napkins, disposable diapers, shorts for adults, tampons, and sanitary cottons. Further, since the polymer of the present invention is less susceptible to deterioration in gel structure even when used for a long period of time, and further, is highly elastic, it can be used as a holding material for various types of gardening and a cut-off material for civil engineering works and construction, and further can be expected to be applied to cosmetics wherein importance is attached to elasticity, water absorption and gas permeability.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the accompanying drawings and the description thereof, which are given by way of illustration only, and thus are not limitative of the present invention.

DETAILED DESCRIPTION OF THE INVENTION

Figure 1:
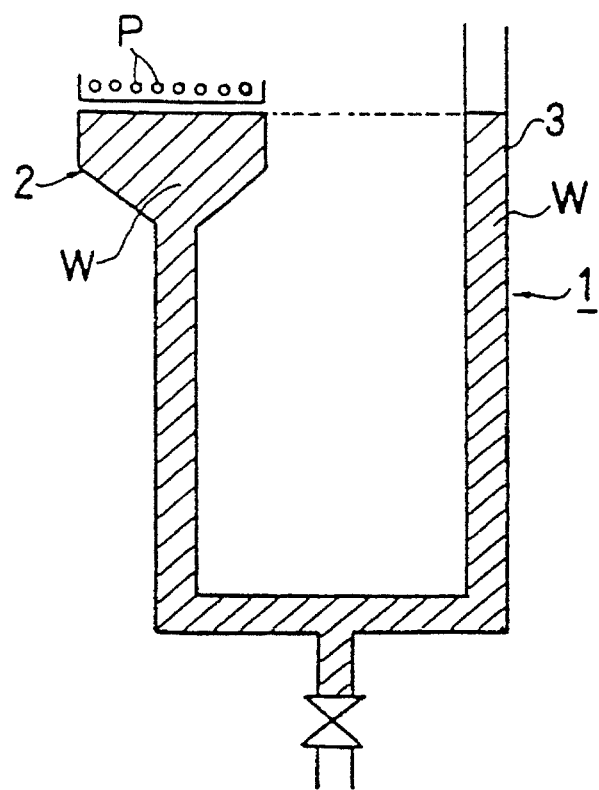
FIG. 1 is a schematic view of an apparatus for measuring the water absorption as a measure of the water absorption rate and used in the Examples and Comparative Examples.

The process for producing polymer particles with an irregular shape according to the present invention will now be described. In the description, "%" is "% by weight" unless otherwise specified.

Preferable examples of the water-soluble polymerizable monomer to be used in the present invention include vinyl monomers having a polymerizable unsaturated group, such as olefinically unsaturated carboxylic acids and salts thereof, olefinically unsaturated carboxylic acid esters, olefinically unsaturated sulfonic acids and salts thereof, olefinically unsaturated phosphoric acids and salts thereof, olefinically unsaturated amines, olefinically unsaturated ammonium salts and olefinically unsaturated amides. Among them, olefinically unsaturated carboxylic acids or salts thereof are particularly preferred in the present invention.

Examples of the olefinically unsaturated carboxylic acids and salts thereof include acrylic acid, methacrylic acid, maleic acid, fumaric acid and alkali salts thereof. Examples of the olefinically unsaturated carboxylic acid esters include methoxypolyethylene glycol (meth)acrylate, phenoxypolyethylene glycol (meth)acrylate and hydroxyethyl (meth)acrylate. Examples of the olefinically unsaturated sulfonic acid and salts thereof include (meth)acrylamidomethylpropanesulfonic acid and allylsulfonic acid and alkali salts thereof. Examples of the olefinically unsaturated phosphoric acids and salts thereof include (meth)acryloyl(poly)oxyethylenephosphoric esters and alkali salts thereof. Examples of the olefinically unsaturated amines include dimethylaminoethyl (meth)-acrylate. Examples of the olefinically unsaturated ammonium salts include (meth)acrylolyloxyethylenetrimethylammonium halide. Examples of the olefinically unsaturated amides include (meth)acrylamide derivatives and vinylmethylacetoacetamides, such as (meth)acrylamide, methyl(meth)acrylamide, ethyl(meth)acrylamide and propyl(meth)acrylamide. They may be used alone or in the form of a mixture of two or more of them. Examples of the alkali salts include alkali metal salts, alkaline earth metal salts and ammonium salts.

The concentration of the water-soluble polymerizable monomer in an aqueous solution thereof is preferably 1 to 70%, still preferably 10 to 60%.

In the present invention, examples of the hydrophobic organic solvent inert to the polymerization include aliphatic hydrocarbons such as n-pentane, cyclopentane, n-hexane, cyclohexane, n-heptane and methylcyclohexane, aromatic hydrocarbons such as benzene and toluene, aliphatic alcohols having 4 to 6 carbon atoms, such as n-butyl alcohol and n-amyl alcohol, aliphatic ketones such as methyl ethyl ketone, and aliphatic esters such as ethyl acetate. These solvents may be used alone or in the form of a mixture of two or more of them.

The amount of the hydrophobic organic solvent used preferably ranges from 50 to 500% based on the aqueous solution of the water-soluble polymerizable monomer.

Preferable examples of the anionic surfactant to be used in the present invention include surfactants having at least one anionic group, such as a $SO_3^{2-}$, $SO_4^{2-}$, phosphate, or carboxylate group. Especially, an anionic surfactant having at least one $SO_3^{2-}$ or $SO_4^{2-}$ group is particularly preferred.

Particularly preferred examples of the surfactant having at least one $SO_3^{2-}$ or $SO_4^{2-}$ group include anionic surfactants represented by the following general formula (I).

$$R_1\text{—}X\text{—}SO_3M \qquad (I)$$

wherein $R_1$ stands for an alkyl group, an alkenyl group or an alkylaryl group each having 6 to 22 carbon atoms, X stands for a moiety having at least one hydrophilic group selected from among an oxygen atom, an ether oxygen, an ester group, an amide group, an ionic group and hydroxyl group, and M stands for an alkali metal, an alkaline earth metal, an ammonium compound or a hydrogen atom.

Examples of the anionic surfactant represented by the general formula (I) include compounds having a sulfo group, such as alkylsulfuric esters, sulfuric esters of polyoxyethylene alkyl ether, sulfuric esters of alkyl glyceryl ether, sulfosuccinic esters of polyoxyethylene alkyl ether, alkylsulfosuccinamides, and α-sulfo fatty acids, and alkali metal salts, alkaline earth metal salts and ammonium salts thereof.

Further, in the present invention, among the compounds represented by the general formula (I), surfactants represented by the following formula (II) are preferred:

$$R_2\text{—}O\text{—}(CH_2CH_2O)_n\text{—}SO_3M \qquad (II)$$

wherein $R_2$ stands for an alkyl group, an alkenyl group or an alkylaryl group each having 6 to 22 carbon atoms, M stands for an alkali metal, an alkaline earth metal, an ammonium compound or a hydrogen atom, and n is 0 to 22, on the average.

Although a satisfactory effect can be attained even when the anionic surfactants are used alone, they may be used in the form of a mixture of two or more of them.

The effect of the anionic surfactant can be attained even when the amount of the anionic surfactant used is small, and this amount preferably ranges from 0.01 to 10%, still preferably from 0.02 to 5%, more preferably from 0.05 to 5% based on the water-soluble polymerizable monomer.

The water-soluble polymerizable monomer can be polymerized in a system comprising a hydrophobic organic solvent inert to the polymerization and an aqueous solution of the water-soluble polymerizable monomer, for example, by the following processes (1) to (4):

(1) a process comprising mixing an aqueous solution of a water-soluble polymerizable monomer with a hydrophobic organic solvent at once and then polymerizing the monomer (batch polymerization);

(2) a process comprising conducting polymerization successively while dropwise adding an aqueous solution of a water-soluble polymerizable monomer to a hydrophobic organic solvent (successive polymerization);

(3) a process comprising conducting polymerization while dropwise adding a mixed solution produced by previously mixing or dispersing an aqueous solution of a water-soluble polymerizable monomer in part of a hydrophobic organic solvent to a hydrophobic organic solvent (predispersion); and (4) a process wherein the processes (1) to (3) are used in combination.

In conducting the polymerization, the anionic surfactant is incorporated in the reaction system by, for example, the following methods (1) to (4):

(1) a method wherein an anionic surfactant is previously dispersed in a hydrophobic organic solvent;

(2) a method wherein an anionic surfactant is previously dissolved or dispersed in an aqueous solution of a water-soluble polymerizable monomer;

(3) a method wherein an anionic surfactant is gradually added while conducting the polymerization; and (4) a method wherein the methods (1) to (3) are used in combination.

In conducting the polymerization, it is preferred to use a polymerization initiator. There is no particular limitation on the polymerization initiator so far as it is a water-soluble free-radical initiator, and examples thereof include ketone peroxides such as methyl ethyl ketone peroxide and methyl isobutyl ketone peroxide, dialkyl peroxides such as di-tert-butyl peroxide and tert-butyl cumyl peroxide, alkyl peroxy esters such as tert-butyl peroxyacetate, tert-butyl peroxyisobutyrate and tert-butyl peroxypivalate, hydrogen peroxide, persulfates such as potassium persulfate and ammonium persulfate, perchlorates such as potassium perchlorate and sodium perchlorate, halogenic acid salts such as potassium chlorate and potassium bromate, and azo compounds such as 2-(carbamoylazo)isobutyronitrile, 2,2-azobis(N,N'-dimethyleneisobutylamidine) dihydrochloride, 2,2'-azobis(2-amidinopropane) dihydrochloride, 2,2'-azobis(N,N'-dimethyleneisobutylamidine), 4,4'-azobis(4-cyanopentanoic acid), azobisisobutyronitrile, 2,2'-azobis(4-methoxy-2,4-dimethylvaleronitrile), (1-phenylethyl)azodiphenylmethane, dimethyl 2, 2'-azobisisobutyrate, 2,2'-azobis(2-methylbutyronitrile), 1,1'-azobis(1-cyclohexanecarbonitrile), 2,2'-azobis(2, 4,4'-trimethylpentane), 2-phenylazo-2,4-dimethyl-4-methoxyvaleronitrile and 2,2'-azobis(2-methylpropane). They may be used alone or in the form of a mixture of two or more of them.

The amount of the polymerization initiator used usually ranges from 0.01 to 10%, preferably from 0.02 to 5%, based on the water-soluble polymerizable monomer.

Although there is no particular limitation on the method for adding the polymerization initiator, it is preferred to previously add the polymerization initiator to the aqueous solution of the polymerizable water-soluble monomer.

In conducting the polymerization, the polymerization temperature usually ranges from 20° to 120° C., preferably from 40° to 100° C. When the polymerization temperature exceeds 120° C., the degree of crosslinking is so extremely enhanced that the absorption capability of the polymer lowers. On the other hand, when the polymerization temperature is below 20° C., the polymerization rate becomes unfavorably very low.

In the present invention, it is preferred that the water-soluble polymerizable monomer be subjected to either homopolymerization by itself or copolymerization. It is also possible to use the water-soluble polymerizable monomer in combination with a water-insoluble monomer copolymerizable therewith, for example, a monomeric ester of an alkyl group having 1 to 22 carbon atoms with an unsaturated carboxylic acid such as acrylic, methacrylic, maleic or fumaric acid, which is used in an amount of 50% or less based on the whole monomer.

Besides the above-described hydrophobic solvent, an amphipathic solvent may be added so far as the amount of use thereof does not exceed that of the hydrophobic solvent. Examples of the amphipathic solvent include alcohols such as methanol, ethanol, propanol and 2-propanol, ketones such as acetone, and ethers such as tetrahydrofuran and dioxane.

Further, besides the anionic surfactant, nonionic surfactants, cationic surfactants, amphoteric surfactants, polymeric dispersants, etc., may be used in combination with the anionic surfactant in an amount of preferably 100 parts by weight or less based on 100 parts by weight of the anionic surfactant.

In the present invention, a known crosslinking agent may be used before, during or after the polymerization. Examples of the crosslinking agent include polyallyl compounds such as N,N-diallyl(meth)-acrylamide, diallylamine, diallyl phthalate, diallyl maleate, diallyl terephthalate, triallyl cyanurate and triallyl phosphate, polyvinyl compounds such as divinylbenzene, N,N-methylenebisacrylamide, ethylene glycol diacrylate, ethylene glycol dimethacrylate and glycerin trimethacrylate, polyglycidyl ethers such as ethylene glycol diglycidyl ether, polyethylene glycol diglycidyl ether and polyglycerin polyglycidyl ether, haloepoxy compounds such as epichlorohydrin and α-methylchlorohydrin, polyaldehydes such as glutaraldehyde and glyoxal, polyols such as glycerin, polyamines such as ethylenediamine, hydroxy vinyl compounds such as 2-hydroxyethyl methacrylate, and inorganic and organometallic salts capable of yielding a polyvalent ion, such as those of calcium, magnesium, zinc and aluminum.

Further, it is also possible to use a modifier, such as a plyoxyethylene alkylphenyl ether.

The amount of use of the crosslinking agent or modifier may be arbitrary according to desired properties of the polymer as the final product and usually preferably ranges from 0.01 to 10%.

The polymer thus produced is dried on a vacuum drier, a fluid drier, etc., immediately after the polymerization or after the removal of the solvent by decantation or centrifugation, and then pulverized or granulated according to need, thus giving polymer particles with an irregular shape.

Although the ionic surfactants have been generally used in the suspension polymerization or emulsion polymerization of hydrophobic monomers because the O/W dispersion is stable, they have hardly been used in the suspension polymerization or emulsion polymerization of water-soluble monomers. Although the mechanism through which the effect of the present invention can be attained has not been elucidated, it is conceivable that, in consideration of the fact that the polymer produced by the conventional O/W type suspension polymerization or emulsion polymerization is a spherical polymer having a uniform shape, the polymerization of the water-soluble monomer proceeds in a somewhat unstable W/O system because it is conducted in the presence of an anionic surfactant, so that the produced polymer has many voids and an irregular shape and holds a suitable particle diameter by virtue of the effect of the anionic group.

The present invention will now be described in more detail with reference to the following Examples and Comparative Examples, though it is not limited to these Examples only.

In the Examples 4–17 and Comparative Examples 1–3, the following tests were conducted.

[Method for measuring equilibrium swelling water absorption of the polymer]

1 g of the polymer was dispersed in a large excess of physiological saline (0.9% saline) to swell the polymer until the absorption reaches the equilibrium swelling state. Then, the physiological saline was filtered off through an 80-mesh gauze, the weight (W) of the resultant swollen polymer was measured, and this value was divided by the weight ($W_0$) of the polymer before the water absorption to provide a $W/W_0$ value as the equilibrium swelling water absorption (g/g).

[Method for measuring water absorption as measure of absorption rate of the polymer]

Use was made of an apparatus (Demand Wettability Tester) generally known as a device for practicing the DW test and shown in FIG. 1. As shown in FIG. 1, 0.3 g of polymer P was spread on a polymer spreading stand 2 (a stand wherein No. 2 filter paper having a diameter of 70 mmØ was put on a glass filter No. 1) set in such a manner that the levels of the physiological saline W are equal to each other. The absorption at the time when the polymer was spread was taken as 0 (zero), and the absorption 30 sec after the spreading of the polymer was measured by reading the graduation of a buret indicating the degree of lowering in the level of the physiological saline W. The measured value was taken as the water absorption (ml) as a measure of the water absorption rate.

[Method for measuring passing rate of physiological saline (factor showing evaluation of gel blocking tendency) of the polymer]

Figure 2:
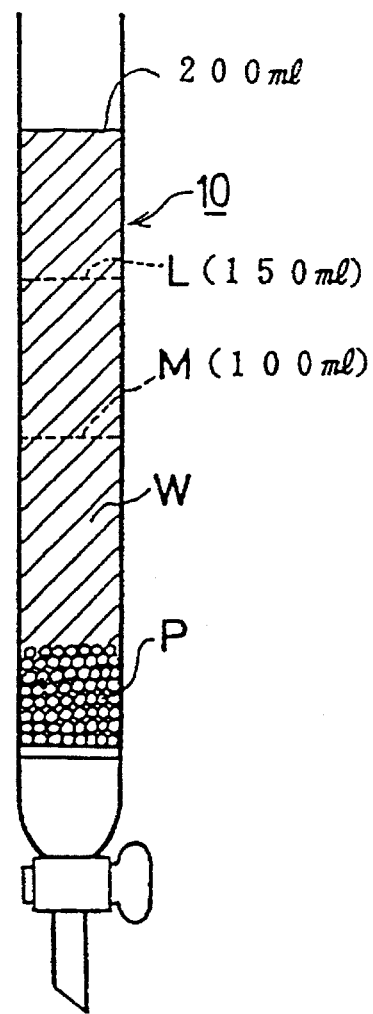
FIG. 2 is a schematic view of an apparatus for measuring the physiological saline and used in the Examples and Comparative Examples.

0.5 g of the polymer was packed in an apparatus 10 (a buret comprising a glass cylindrical tube equipped with a cock and having an inner diameter of 25.6 mm and a length of about 500 mm (a cylindrical portion)) shown in FIG. 2, and swollen with an excess of physiological saline until the swelling reached equilibrium. The level of the physiological saline was adjusted to a position corresponding to 200 ml from the bottom, and the cock was closed. After the polymer P was sufficiently settled as shown in the figure, the cock was opened to measure the time taken for the physiological saline W to pass through between two marked lines shown in the figure, that is, marked line L (a position corresponding to 150 ml from the bottom) and marked line M (a position corresponding to 100 ml from the bottom) (amount of liquid: 50 ml), and the amount (ml) of liquid between the marked lines was divided by the measured time (min) to give the solution passing rate (ml/min).

[Method for measuring the average particle diameter]

100 g of polymer was classified with the use of JIS sieve and the average particle diameter of the polymer was measured according to the weight ratio of each fraction.

[EXAMPLE 1]

72.1 g of acrylic acid is diluted with 18.0 g of water and neutralized with 98.9 g of a 30 wt. % aqueous sodium hydroxide solution under cooling, and 10.7 g of a 2.8 wt. % aqueous 2,2'-azobis(2-amidinopropane) dihydrochloride solution is added thereto to prepare a homogeneous solution as an aqueous monomer/initiator solution.

Separately, a 500-ml flask equipped with a reflux condenser, a dropping funnel, a stirring rod and a nitrogen gas feed pipe is charged with 283 ml of cyclohexane, and 2.2 g of a 25 wt. % aqueous solution of sodium salt of polyoxyethylene dodecyl ether sulfate [average number of moles of addition of ethylene oxide: 2] is added thereto. They are stirred (at 300 rpm) and dispersed in each other, and the flask is purged with nitrogen and heated to 75° C. The above-described aqueous monomer/initiator solution is dropwise added thereto over a period of 30 min. After the completion of the addition, the system is subjected to polymerization with stirring at 75° C. for 1.5 h and at 80° C. for 4 h.

After the completion of the polymerization, the product is fractionated and dried under reduced pressure to provide 88.4 g of a polymer of acrylic acid (sodium salt). The resultant polymer is a granular material having a distorted shape with an average particle diameter of 400 μm as measured by sieving, and a bulk density of 0.41 g/ml. The surface of the polymer particle has such a structure that particles having an irregular shape of several microns to 20 μm in size are fused to each other, and the unevenness of the surface is very significant.

[EXAMPLE 2]

71.1 g of acrylamide is dissolved in 150 g of water, and 10.7 g of a 2.8 wt. % aqueous 2,2'-azobis(2-amidinopropane) dihydrochloride solution is added thereto to prepare a homogeneous solution as an aqueous monomer/initiator solution. Thereafter, the procedure of Example 1 is repeated, except that hexane is used as the solvent instead of cyclohexane, thereby providing 68 g of an acrylamide polymer. The resultant polymer is a granular material having a distorted shape of 500 μm in the average particle diameter as measured by sieving and a bulk density of 0.40 g/ml. The surface of the polymer particle has such a structure that particles having an irregular shape of several microns to 20 μm in size are fused to each other, and the unevenness of the surface is very significant.

[EXAMPLE 3]

106.6 g of sodium acrylamido methylpropanesulfonate is dissolved in 150 g of water, and 10.7 g of a 2.8 wt. % aqueous 2,2'-azobis(2-amidinopropane) dihydrochloride solution is added thereto to prepare a homogeneous solution as an aqueous monomer/initiator solution. Thereafter, the procedure of Example 1 is repeated to provide 88.4 g of a sodium acrylamidomethylpropanesulfonate polymer of 95 g [sic]. The resultant polymer is a granular material having a distorted shape with an average particle diameter of 500 μm as measured by sieving and a bulk density of 0.48 g/ml. The surface of the polymer particle has such a structure that particles having an irregular shape of several microns to 20 μm in size are fused to each other, and the unevenness of the surface is very significant.

[EXAMPLE 4]

72.1 g of acrylic acid was diluted with 32.0 g of water and neutralized with 98.9 g of a 30 wt. % aqueous sodium hydroxide solution under cooling, and 10.7 g of a 2.8 wt. % aqueous potassium persulfate solution was added thereto to prepare a homogeneous solution as an aqueous monomer/ initiator solution.

Separately, a 500-ml flask equipped with a reflux condenser, a dropping funnel, a stirring rod and a nitrogen gas feed pipe was charged with 283 ml of cyclohexane, and 1.5 g of a 25 wt. % aqueous solution of sodium salt of polyoxyethylene dodecyl ether sulfate [average number of moles of addition of ethylene oxide: 3] was added thereto. They were stirred (at 300 rpm) and dispersed in each other, and the flask was purged with nitrogen and heated to 75° C. The above-described aqueous monomer/initiator solution was dropwise added thereto over a period of 30 min. In this case, 0.058 g of ethylene glycol diglycidyl ether was simultaneously dropwise added as an epoxy bifunctional crosslinking agent in portions through a syringe. After the completion of the dropwise addition, the system was subjected to polymerization with stirring at 75° C. for 1.5 h and at 80° C. for 4 h. After the completion of the polymerization, the product was fractionated and dried under reduced pressure to provide 88.4 g of a polymer of acrylic acid (sodium salt). The resultant polymer was a granular material having a distorted shape of 400 µm in the average particle diameter as measured by sieving and a bulk density of 0.41 g/ml. The surface of the polymer particle had such a structure that particles having an irregular shape of several microns to 20 µm in size were fused to each other, and the unevenness of the surface was very significant.

The resultant polymer was subjected to measurement of the equilibrium swelling water absorption, water absorption as a measure of the water absorption rate and physiological saline passing rate. The results are given in Table 1.

[EXAMPLE 5]

36.1 g of acrylic acid was dissolved in 16.0 g of water and neutralized with 53.0 g of a 30 wt. % aqueous sodium hydroxide solution under cooling. Thereafter, 101.3 g of a 40% aqueous sodium acrylamidomethylpropanesulfonate solution was added thereto, and 10.7 g of a 2.8 wt. % aqueous potassium persulfate solution was added thereto to prepare a homogeneous solution as an aqueous monomer/initiator solution. Thereafter, the procedure of Example 4 was repeated to provide 93.5 g of a sodium acrylate/sodium acrylamidomethylpropanesulfonate copolymer. The resultant polymer was a granular material having a distorted shape of 550 µm in the average particle diameter as measured by sieving and a bulk density of 0.45 g/ml.

The resultant polymer was subjected to measurement in the same manner as that of Example 4. The results are given in Table 1.

[EXAMPLE 6]

The procedure of Example 4 was repeated, except a sodium salt of polyoxyethylene tetradecyl ether sulfate [average number of moles of addition of ethylene oxide: 3] was used as a dispersant instead of a sodium salt of polyoxyethylene dodecyl ether sulfate, thereby providing a granular material having a remarkably uneven surface and a distorted shape. The bulk density was 0.38 g/ml.

The resultant polymer was subjected to measurement in the same manner as that of Example 4. The results are given in Table 1.

[EXAMPLE 7]

The procedure of Example 4 was repeated, except that a triethanolamine salt of polyoxyethylene dodecyl ether sulfate [average number of moles of addition of ethylene oxide: 3] was used as a dispersant instead of a sodium salt of polyoxyethylene dodecyl ether sulfate, thereby providing a granular material having a remarkably uneven surface and a distorted shape. The bulk density was 0.41 g/ml.

The resultant polymer was subjected to measurement in the same manner as that of Example 4. The results are given in Table 1.

[EXAMPLE 8]

The procedure of Example 4 was repeated, except that a sodium salt of dodecyl glyceryl ether sulfate [average number of sulfate groups: 1.5] was used as a dispersant instead of a sodium salt of polyoxyethylene dodecyl ether sulfate, thereby providing a granular material having a remarkably uneven surface and a distorted shape. The bulk density was 0.45 g/ml.

The resultant polymer was subjected to measurement in the same manner as that of Example 4. The results are given in Table 1.

[EXAMPLE 9]

The procedure of Example 4 was repeated, except that sodium salt of polyoxyethylene nonylphenyl ether sulfate [average number of moles of addition of ethylene oxide: 3] was used as a dispersant instead of sodium salt of polyoxyethylene dodecyl ether sulfate, thereby providing a granular material having a remarkably uneven surface and a distorted shape. The bulk density was 0.52 g/ml.

The resultant polymer was subjected to measurement in the same manner as that of Example 4. The results are given in Table 1.

[EXAMPLE 10]

The procedure of Example 4 was repeated, except that a sodium salt of dodecyl ether sulfate was used instead of a sodium salt of polyoxyethylene dodecyl ether sulfate, thereby providing a granular material having a remarkably uneven surface and a distorted shape. The bulk density was 0.47 g/ml.

The resultant polymer was subjected to measurement in the same manner as that of Example 4. The results are given in Table 1.

[EXAMPLE 11]

The procedure of Example 4 was repeated, except that a sodium salt of tri(oxypropylene) dodecyl ether sulfate [number of moles of addition of propylene oxide: 3] was used instead of a sodium salt of polyoxyethylene dodecyl ether sulfate, thereby providing a granular material having a remarkably uneven surface and a distorted shape. The bulk density was 0.55 g/ml.

The resultant polymer was subjected to measurement in the same manner as that of Example 4. The results are given in Table 1.

[EXAMPLE 12]

The procedure of Example 4 was repeated, except that a sodium salt of dodecylsulfosuccinamide was used as the dispersant instead of a sodium salt of polyoxyethylene dodecyl ether sulfate, thereby providing a granular material having a remarkably uneven surface and a distorted shape. The bulk density was 0.51 g/ml.

The resultant polymer was subjected to measurement in the same manner as that of Example 4. The results are given in Table 1.

[EXAMPLE 13]

The procedure of Example 4 was repeated, except that a sodium salt of polyoxyethylene dodecylsulfosuccinate [average number of moles of addition of ethylene oxide: 3] was used as the dispersant instead of a sodium salt of polyoxyethylene dodecyl ether sulfate, thereby providing a granular material having a remarkably uneven surface and a distorted shape. The bulk density was 0.53 g/ml.

The resultant polymer was subjected to measurement in the same manner as that of Example 4. The results are given in Table 1.

[EXAMPLE 14]

72.1 g of acrylic acid was diluted with 18.0 g of water and neutralized with 98.9 g of a 30 wt. % aqueous sodium hydroxide solution under cooling, and 10.7 g of a 2.8 wt. % aqueous potassium persulfate solution was added thereto to prepare a homogeneous solution.

Separately, a 500-ml flask equipped with a reflux condenser, a dropping funnel, a stirring rod and a nitrogen gas feed pipe was charged with 283 ml of cyclohexane, and 2.2 g of a 25 wt. % aqueous solution of a sodium salt of polyoxyethylene dodecyl ether sulfate [average number of a moles of addition of ethylene oxide: 2] was added thereto. They were stirred (at 300 rpm) and dispersed in each other, and the flask was purged with nitrogen and heated to 75° C. The above-described aqueous monomer/initiator solution was dropwise added thereto over a period of 30 min. After the completion of the dropwise addition, the system was subjected to polymerization with stirring at 75° C. for 1.5 h and at 80° C. for 4 h. In this case, only water was continuously removed from an azeotropic reflux liquid comprising cyclohexane and water. When the water content of the acrylic acid (sodium salt) polymer gel reached 30% by weight, 0.18 g of an epoxy bifunctional crosslinking agent (ethylene glycol diglycidyl ether) was added to conduct a reaction for 30 min, and a partially crosslinked acrylic acid (sodium salt) polymer was taken out and dried. The resultant granular material was fractionated and dried under reduced pressure to provide 88.0 g of an acrylic acid (sodium salt) polymer. The resultant polymer was a granular material having a distorted shape of 400 μm in the average particle diameter as measured by sieving and a bulk density of 0.42 g/ml.

The resultant polymer was subjected to measurement in the same manner as that of Example 4. The results are given in Table 1.

[EXAMPLE 15]

The procedure of Example 14 was repeated, except that sodium salt of polyoxyethylene decyl ether sulfate [average number of moles of addition of ethylene oxide: 7] was used as the dispersant instead of sodium salt of polyoxyethylene dodecyl ether sulfate, thereby providing a granular material having a remarkably uneven surface and a distorted shape. The bulk density was 0.39 g/ml.

The resultant polymer was subjected to measurement in the same manner as that of Example 4. The results are given in Table 1.

[EXAMPLE 16]

The procedure of Example 14 was repeated, except that a sodium salt of polyoxyethylene octyl ether sulfate [average number of moles of addition of ethylene oxide: 4] was used as the dispersant instead of a sodium salt of polyoxyethylene dodecyl ether sulfate, thereby providing a granular material having a remarkably uneven surface and a distorted shape. The bulk density was 0.45 g/ml.

The resultant polymer was subjected to measurement in the same manner as that of Example 4. The results are given in Table 1.

[EXAMPLE 17]

The procedure of Example 14 was repeated, except that a sodium salt of polyoxyethylene stearyl ether sulfate [average number of moles of addition of ethylene oxide: 10] was used as the dispersant instead of a sodium salt of polyoxyethylene dodecyl ether sulfate, thereby providing a granular material having a remarkably uneven surface and a distorted shape. The bulk density was 0.49 g/ml.

The resultant polymer was subjected to measurement in the same manner as that of Example 4. The results are given in Table 1.

[COMPARATIVE EXAMPLE 1]

A polymer was produced in the same manner as that of Example 4, except that 0.9 g of ethylcellulose was used as the dispersant instead of an aqueous solution (2.2 g) of a sodium salt of polyoxyethylene dodecyl ether sulfate. The resultant polymer of acrylic acid (sodium salt) produced in this system was spherical and had a particle diameter of 10 to 400 μm and a bulk density of 0.94 g/ml.

The resultant polymer was subjected to measurement in the same manner as that of Example 4. The results are given in Table 1.

[COMPARATIVE EXAMPLE 2]

A polymer was prepared in the same manner as that of Example 4, except that 2.9 g of sorbitan monostearate (Span 60) was used as the dispersant instead of an aqueous solution of a sodium salt of polyoxyethylene dodecyl ether sulfate. The polymer of acrylic acid (sodium salt) produced in this system comprised a mixture of spherical particles having a particle diameter in the range of from 10 to 100 μm and secondary particles comprising an aggregate of the spherical particles and having a particle diameter in the range of from 50 to 1000 μm and had a bulk density of 0.65 g/ml. When the resultant aggregate was put into physiological saline, part of the secondary particles returned to primary particles alone without difficulty.

The resultant polymer was subjected to measurement in the same manner as that of Example 4. The results are given in Table 1.

[COMPARATIVE EXAMPLE 3]

A polymer was produced in the same manner as that of Example 14, except that 0.9 g of ethylcellulose was used as the dispersant instead of an aqueous solution of a sodium salt of polyoxyethylene dodecyl ether sulfate. The resultant polymer of acrylic acid (sodium salt) produced in this system was spherical and had a particle diameter of 10 to 400 μm and a bulk density of 0.93 g/ml.

The resultant polymer was subjected to measurement in the same manner as that of Example 4. The results are given in Table 1.

TABLE 1

|  |  | Equilibrium swelling water absorption (g/g) | Water absorption (ml) | Soln. passing rate (ml/min) |
|---|---|---|---|---|
| Ex. | 4 | 58 | 4.3 | 16.6 |
|  | 5 | 57 | 4.2 | 12.2 |
|  | 6 | 55 | 3.6 | 13.5 |
|  | 7 | 57 | 3.7 | 12.6 |
|  | 8 | 56 | 3.9 | 14.1 |

TABLE 1-continued

|  |  | Equilibrium swelling water absorption (g/g) | Water absorption (ml) | Soln. passing rate (ml/min) |
|---|---|---|---|---|
|  | 9 | 57 | 3.6 | 12.3 |
|  | 10 | 58 | 3.9 | 14.4 |
|  | 11 | 56 | 4.2 | 13.2 |
|  | 12 | 56 | 4.1 | 15.2 |
|  | 13 | 55 | 3.8 | 12.4 |
|  | 14 | 55 | 7.5 | 35.2 |
|  | 15 | 56 | 7.8 | 36.4 |
|  | 16 | 55 | 6.4 | 28.3 |
|  | 17 | 54 | 5.6 | 23.4 |
| Comp. Ex. | 1 | 53 | 2.7 | 2.3 |
|  | 2 | 55 | 3.5 | 1.5 |
|  | 3 | 53 | 2.8 | 5.4 |

What is claims is:

1. A process for producing polymer particles with an irregular shape, comprising polymerizing at a temperature of from 20° to 120° C. a water-soluble polymerizable monomer in a reverse phase polymerization system comprising (a) a hydrophobic organic solvent inert to the polymerization, (b) an aqueous solution of said water-soluble polymerizable monomer, wherein the concentration of said water-soluble polymerizable monomer in said aqueous solution is 1 to 70% by weight, and (c) a surfactant consisting essentially of an anionic surfactant, wherein said anionic surfactant comprises an anionic surfactant having at least one $SO_3^{2-}$ or $SO_4^{2-}$ group.

2. The process for producing polymer particles with an irregular shape according to claim 1, wherein said anionic surfactant comprises an anionic surfactant represented by the following formula (I)

$$R_1\text{—}X\text{—}SO_3M \quad (I)$$

wherein $R_1$ stands for an alkyl group, an alkenyl group or an alkylaryl group, each having 6 to 22 carbon atoms, X stands for a moiety having at least one hydrophilic group selected from the group consisting an oxygen atom, an ether moiety, an ester group, an amide group, an ionic group and a hydroxyl group, and M stands for an alkali metal, an alkaline earth metal, an ammonium ion or a hydrogen atom.

3. The process for producing polymer particles with an irregular shape according to claim 2, wherein the anionic surfactant represented by the formula (I) is an anionic surfactant represented by the following formula (II)

$$R_2\text{—}O\text{—}(CH_2CH_2O)_n\text{—}SO_3M \quad (II)$$

wherein $R_2$ stands for an alkyl group, an alkenyl group or an alkylaryl group each having 6 to 22 carbon atoms, M stands for an alkali metal, an alkaline earth metal, an ammonium ion or a hydrogen atom, and n is a number from 0 to 22, on the average.

4. The process for producing polymer particles with an irregular shape according to claim 1, wherein said water-soluble polymerizable monomer is an olefinically unsaturated carboxylic acid or an alkali salt thereof.

5. The process for producing polymer particles with an irregular shape according to claim 1, wherein said polymer is water absorbent polymer.

6. A process for producing polymer particles with an irregular shape, comprising polymerizing at a temperature of from 20° to 120° C. a water-soluble polymerizable monomer in a reverse phase polymerization system comprising (a) a hydrophobic organic solvent inert to the polymerization, (b) an aqueous solution of said water-soluble polymerizable monomer, wherein the concentration of said water-soluble polymerizable monomer in said aqueous solution is 1 to 70% by weight, (c) an anionic surfactant, and (d) a nonionic surfactant in an amount greater than 0, and up to and including 1 part by weight based on 1 part by weight of anionic surfactant.

* * * * *